United States Patent [19]
Voege et al.

[11] Patent Number: 5,485,983
[45] Date of Patent: Jan. 23, 1996

[54] SEAL APPARATUS FOR A FLOW CONTROL VALVE

[75] Inventors: James A. Voege; Richard B. Voege; John S. Voege, all of Carmel, Ind.

[73] Assignee: AMP Corporation, Carmel, Ind.

[21] Appl. No.: 294,622

[22] Filed: Aug. 23, 1994

[51] Int. Cl.$^6$ .............................. F16K 3/32; F16K 51/00
[52] U.S. Cl. .................... 251/206; 251/361; 251/363
[58] Field of Search ................................. 251/359, 900, 251/360, 361, 363, 364, 206, 208

[56] References Cited

U.S. PATENT DOCUMENTS

| | | | |
|---|---|---|---|
| 2,492,006 | 12/1949 | Raybould. | |
| 2,825,590 | 3/1958 | Sutherland. | |
| 2,935,365 | 5/1960 | Dega. | |
| 2,963,261 | 12/1960 | Holl | 251/363 X |
| 3,134,572 | 5/1964 | Glasgow | 251/363 |
| 3,905,608 | 9/1975 | Olsen et al. | |
| 4,083,383 | 4/1978 | Antoniello | 251/363 X |
| 4,303,250 | 12/1981 | Persson. | |
| 4,304,261 | 12/1981 | Forester. | |
| 4,366,947 | 1/1983 | Voege. | |
| 4,513,778 | 4/1985 | Vadasz | 251/363 X |
| 4,531,404 | 7/1985 | Phelps et al. | |
| 4,828,272 | 5/1989 | Pedersen. | |
| 4,942,902 | 7/1990 | Knapp | 251/363 X |
| 4,993,924 | 2/1991 | Mukumoto et al. | |
| 5,074,524 | 12/1991 | Wade | 251/361 X |

Primary Examiner—Martin P. Schwadron
Assistant Examiner—Kevin L. Lee
Attorney, Agent, or Firm—Barnes & Thornburg

[57] ABSTRACT

A gas metering valve is provided for selectively providing a series of different calibrated gas flow rates. The valve includes a valve body having a gas inlet, a gas outlet, a chamber situated between the gas inlet and gas outlet. The valve also includes a metering element located in the chamber. The metering element is formed to include a plurality of passageways for permitting gas flow from the gas inlet to the gas outlet. The metering element is movable relative to the valve body to position a selected passageway in communication with the gas inlet. The valve further includes a seal apparatus including a sealing disk in sliding contact with the metering element. The sealing disk has an aperture formed therethrough aligned with the gas inlet for sealing said chamber against the transmission of gas therethrough except when the metering element is oriented with the selected passageway in registry with the aperture in the sealing disk. The sealing disk is also formed to include a recessed portion surrounding the aperture. The seal apparatus also includes an O-ring located in the recessed portion of the sealing disk for engaging the metering element.

16 Claims, 1 Drawing Sheet

SEAL APPARATUS FOR A FLOW CONTROL VALVE

BACKGROUND AND SUMMARY OF THE INVENTION

This invention relates to calibrated gas metering devices, and particularly those devices applicable to provide a precisely calibrated therapeutic oxygen flow in a portable oxygen supply kit adapted to be carried by an ambulatory patient to supply a prescribed rate of oxygen to such patient. More particularly, the present invention relates to an improved seal apparatus for use in a selective control valve which is used in such metering devices to selectively provide a plurality of accurate oxygen flow rates.

Oxygen supply kits for ambulatory patients are known and in use. They include an indexing control valve which is movable to a plurality of positions, each providing a different flow rate. For example, the control valve can be set to deliver 1, 2, 3, 4, and 5 liters per minute. Such flow rates are obtained by passing the gas at a regulated pressure through metering orifices in a metering disk. In one application, such rates required metering holes having diameters, respectively, of approximately 0.006, 0.009, 0.011, 0.013, and 0.015 inches. The orifices had been formed by drilling these small holes in the metering disk or inserts in the metering disk mechanically or by an EDM process. Such drilling does not provide sufficient accuracy, and when the EDM process is employed, it is necessary to allow a margin of error of plus or minus 10% of the desired flow rate. See, for example, U.S. Pat. No. 3,949,966.

A conventional gas metering valve includes a valve body having an inlet and an outlet with a dividing wall therebetween, the dividing wall including a metering element having a first and second hole therein, which first and second holes intersect and together define a passageway for gas flow from the inlet to the outlet. A ball of a diameter approximately equal to the diameter of the first hole is press-fitted into the first hole so as to be positioned therein solely by the fitting engagement of its surface with the wall of the first hole. The ball is positioned adjacent the intersection of the first and second holes so as to define a region in the passage having a cross-sectional area less than the cross-sectional area of either the first or second hole. By manipulating the position of the ball while monitoring the flow of gas through the passage, the ball can be positioned at a location which will achieve the desired gas flow rate. Desirably, the first hole is several times larger and preferably four or more times larger than the second hole. On the one hand, this facilitates handling and insertion of the ball, and on the other hand, facilitates formation of a gas passage providing the desired small and accurate gas flow rate. A plurality of such first and second holes can be provided, each set of a first and a second hole defining a separate passage for the metered flow of gas from the inlet to the outlet. The passages thus defined are positionable in communication with the gas inlet such that only one such passage can permit the flow of gas therethrough at any one instant in time. A detent means can be provided for assuring appropriate alignment of one of said passages with respect to the gas inlet. For an example of such a gas-metering valve, see U.S. Pat. No. 4,366,947 which is incorporated herein by reference.

The metering element comprises a cylinder, and the first holes are arranged in a circle about the axis of rotation of the cylinder and extend linearly through the cylindrical element parallel to the axis of rotation. The second holes extend radially from the cylindrical surface of the element to the point of intersection with the first holes. The balls are press-fit from one face of the cylinder to the point of intersection of the first and second holes, each ball being positioned at a slightly different location so as to achieve a different flow rate through each passage thus formed.

To assure proper alignment of the cylindrical metering element, a circular race is provided in one end of the element, the race being in registry with the circular arrangement of first holes. A detent means comprising a spring-biased ball is arranged in rolling frictional engagement in the race to effect an arresting action in any rotation of the cylindrical element, the detent means being so situated as to cause selected alignment of a single first and second hole pair to provide a passage between the inlet and outlet of the gas-metering valve.

Conventional gas metering valves include a two piece seal arrangement located between the metering element and the valve body. This two piece sealing arrangement includes a sealing disk and a separate O-ring for holding the sealing disk against the metering element. One problem associated with this conventional arrangement is that the O-ring may be compressed during operation of the valve to restrict or block gas flow from the gas inlet through the aperture of the sealing disk and into the passageway of the metering element.

The improved seal apparatus of the present invention advantageous provides a seal between the movable cylindrical metering element and the valve body. The improved seal apparatus includes a plastic sealing disk having an aperture formed therethrough. The disk is also formed to include a notch or recessed portion surrounding the aperture for receiving an O-ring therein. Therefore, the O-ring is nested within the plastic sealing disk. The improved configuration of the seal apparatus of the present invention advantageously limits compression of the O-ring to a predetermined amount. By limiting compression of the O-ring, the improved seal apparatus of the present invention advantageously reduces the likelihood that the O-ring will block flow of gas from the gas inlet through the aperture formed in the sealing disk and into the passageway of the metering element.

According to one aspect of the invention, an improvement is provided for use in a calibrated gas metering valve including a valve body having a gas inlet and a gas outlet, and a metering element located therebetween. The metering element includes a passageway formed therethrough to permit gas flow through the passageway from the gas inlet to the gas outlet. The improvement comprises a cylindrical sealing disk formed to include an aperture aligned with the passageway and the gas inlet to permit gas flow through the sealing disk. The sealing disk provides a seal between the valve body and the metering element. The sealing disk is formed to include a recessed portion surrounding the aperture. The improvement further includes an O-ring located in the recessed portion of the sealing disk to limit compression of the O-ring to a predetermined amount.

The sealing disk includes an inner wall defining the aperture and an outer wall. In one illustrated embodiment, the recessed portion for receiving the O-ring is formed in the sealing disk adjacent the inner wall. In another illustrated embodiment, the recessed portion for receiving the O-ring is formed in the sealing disk adjacent the outer wall. In another illustrated embodiment, the recessed portion is an annular trough formed in the sealing disk between the inner and outer walls for receiving the O-ring.

According to another aspect of the present invention, a gas metering valve is provided for selectively providing a series of different calibrated gas flow rates. The valve includes a valve body having a gas inlet, a gas outlet, a chamber situated between the gas inlet and gas outlet. The valve also includes a metering element located in the chamber. The metering element is formed to include a plurality of passageways for permitting gas flow from the gas inlet to the gas outlet. The metering element is movable relative to the valve body to position a selected passageway in communication with the gas inlet. The valve further includes a seal apparatus including a sealing disk in sliding contact with the movable metering element. The sealing disk has an aperture formed therethrough aligned with the gas inlet for sealing said chamber against the transmission of gas therethrough except when the metering element is oriented with the selected passageway in registry with the aperture in the sealing disk. The sealing disk is also formed to include a recessed portion surrounding the aperture. The seal apparatus also includes an O-ring located in the recessed portion of the sealing disk for engaging the metering element to assure constant frictional engagement between the metering element and the sealing disk.

In the illustrated embodiment, the metering element is cylindrical and rotatable within the chamber of the valve body about an axis of rotation. The plurality of passageways are arranged about the axis of rotation and extending linearly through the cylindrical metering element parallel to the axis of rotation.

Additional objects, features, and advantages of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
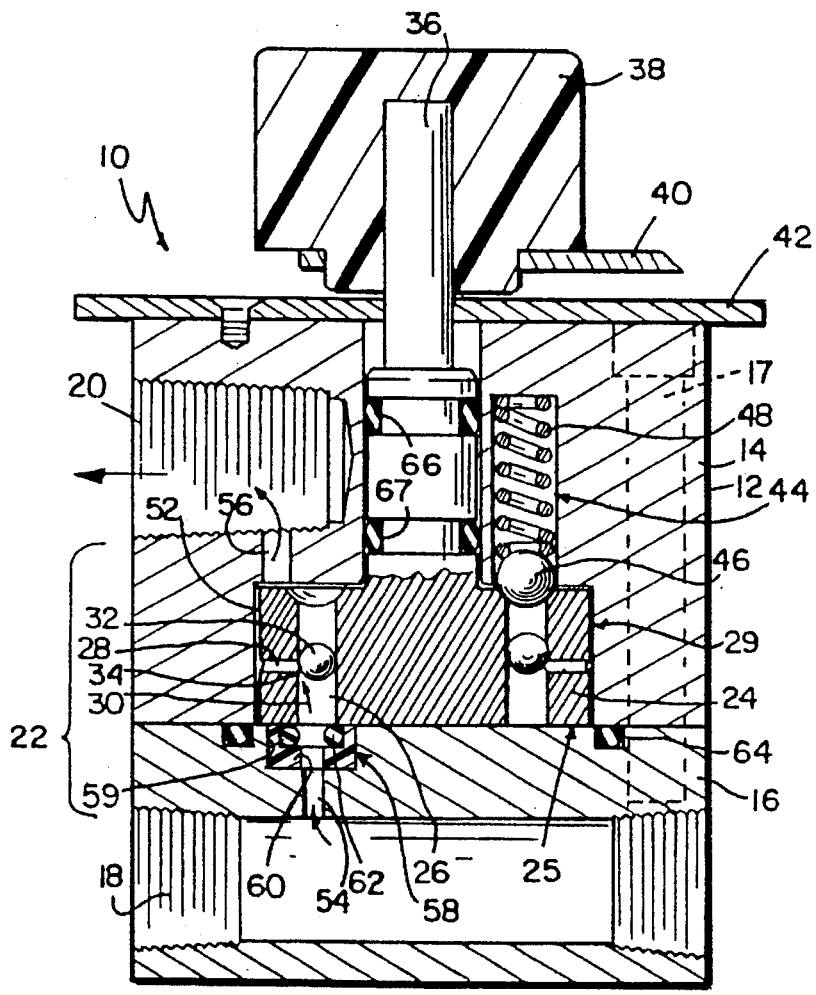
FIG. 1 is a sectional view taken through a calibrated gas metering apparatus including an improved seal apparatus according to the present invention.

The valve 10 shown in FIG. 1 comprises a valve housing 12 illustrated to include a top body 14 and a bottom body 16 secured to the top body 14 by screw-threaded studs 17. The valve housing 12 includes a gas inlet 18 and a gas outlet 20 separated by a dividing wall region 22 including a gas-metering element 24. The gas-metering element includes a first hole 26 and a second hole 28 which intersects the first hole 26. By way of example, the first hole may be of 0.124 inch diameter and the second of 0.020 inch diameter. The first hole 26 and second hole 28 together define a passage 30 for gas to flow from the gas inlet 18 to the gas outlet 20. A ball 32 of a diameter approximately equal to the diameter of the first hole 26 of 0.125 inch diameter in the above example is press-fitted into the first hole 26 so as to be solidly positioned therein solely by the fitting engagement of its surface with the wall of the first hole 26. The ball 32 is positioned adjacent the intersection of the first hole 26 and second hole 28 so as to define a restricted opening or region 34 in the passage 30 having a cross-sectional area less than the cross-sectional area of either the first hole 26 or the second hole 28. It is this restricted region 34 which performs the metering function in the present gas-metering valve 10.

The metering element 24 shown is cylindrical in shape and includes a plurality of such first and second holes as illustrated further in U.S. Pat. No. 4,366,947 incorporated herein by reference. The metering element is adapted to be selectively moved to a plurality of metering positions to selectively provide a series of different gas-flow rates. The first holes 26 are arranged in a circle about the axis of rotation 35, the holes 26 extending linearly through the cylindrical element 24 parallel to the axis of rotation 35. The second holes 28 extend radially from the cylindrical surface 29 of element 24 to the point of intersection of the second hole 28 with the first hole 26.

The element 24 is rotatable about axis 35 by means of shaft 36 projecting axially upward beyond the upper surface of top body 14. A knob 38 is fixed to shaft 36, the knob 38 including an indicator means 40 which, together with appropriate markings on face plate 42, indicate the angular position of element 24.

The valve further comprises a detent means 44 for arresting the movement of the metering element 24 with respect to the valve body 12 so as to assure registry of one of the passages 30 with the gas inlet 18. The detent means 44 comprises a ball 46 and biasing spring 48 which forces the ball 46 into rolling frictional engagement with a circular race provided on one end of the cylindrical valve element 24. The race is in registry with the circular arrangement of first holes 26 such that when the biased ball 46 contacts the top of a first hole 26, the biased ball descends downward sufficient to releasably lockingly engage element 24 with respect to body 12.

Figure 2:
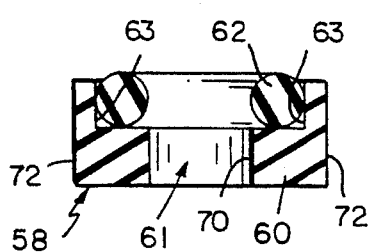
FIG. 2 is an enlarged sectional view of the seal apparatus of FIG. 1 further illustrating details of a sealing disk having an O-ring mounted within a recessed portion formed adjacent an inner wall of the sealing disk.

The cylindrical element 24 is rotatably positioned within a chamber 52 which is situated between the gas inlet 18 and the gas outlet 20. A first aperture 54 is provided between the chamber 52 and the gas inlet 18. A second aperture 56 is provided between chamber 52 and gas outlet 20. The first aperture 54 includes a seal apparatus 58 of the present invention located in recessed portion 59 of bottom body 16 in sliding contact with the gas-metering element 24. The seal apparatus 58 includes a plastic cylindrical sealing disk 60 having an aperture 61 formed therethrough as illustrated in FIG. 2. The sealing disk 60 is preferably composed of a material having a very low frictional coefficient as well as self-lubricating qualities such as tetrafluoroethylene or the like. Illustratively sealing disk 60 is a model number 10146-R Kel-F disk available from Zatkoff in Holland, Ohio. Sealing disk 60 of FIGS. 1 and 2 is formed to include a notch or annular recessed portion 63. An O-ring 62 is located within recessed portion 63 formed in sealing disk 60. Preferably, O-ring 62 is a carboxylated nitrile O-ring available from Zatkoff. O-ring 62 engages metering element 24 to hold sealing disk 60 against bottom body 16. Sealing disk 60 also engages a lower face 25 of metering element 24. Sealing disk 60 is in constant frictional engagement with the lower face 25 of gas-metering element 24. The chamber 52 is further sealed by O-ring 64 located in an upper surface of the bottom body 16 surrounding the chamber 52 and by O-rings 66 and 67 surrounding shaft 36.

Further details of the seal apparatus 58 are illustrated in FIG. 2. FIG. 2 illustrates sealing disk 60 having an inner sidewall 70 and an outer sidewall 72. Inner sidewall 70 defines aperture 61 of sealing disk 60 to permit gas to pass from inlet 18 into a selected hole 26 of metering element 24. Recessed portion 63 is formed adjacent inner sidewall 70 using a suitable cutting tool. Alternatively, sealing disk 60 can be initially formed to include recessed portion 63. O-ring 62 is located within recessed portion 63 of sealing disk 60. Advantageous, positioning O-ring 62 in notched section 63 provides an improved seal apparatus 58. In prior metering valve assemblies, compression of the O-ring may result in a closing of a flow passage 54. The improved configuration of the present invention limits compression of O-ring 62 to a predetermined amount. Therefore, the present invention reduces the likelihood that O-ring seal 62 will be compressed to block flow passage 54.

Figure 3:
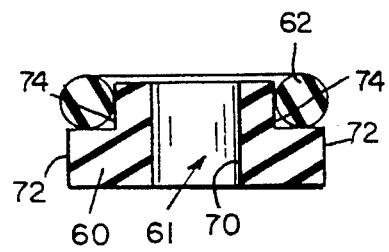
FIG. 3 is a sectional view of a second embodiment of the seal apparatus of the present invention in which the O-ring is located within a recessed portion formed around an outer periphery of the sealing disk adjacent an outer wall.

Another embodiment of the present invention is illustrated in FIG. 3. Those elements referenced by numbers identical to FIG. 2 perform the same or similar function. In the FIG. 3 embodiment, an annular notch or recessed portion 74 is formed around an outer periphery of sealing disk 60 adjacent outer sidewall 72. An O-ring 62 is located within outer notched section 74.

Figure 4:
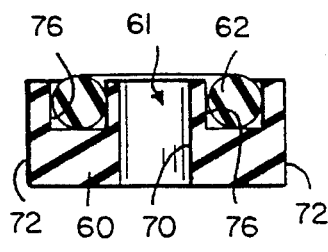
FIG. 4 is a sectional view taken through a third embodiment of the present invention in which an O-ring seal is located within a trough formed between an inner sidewall and an outer sidewall of the sealing disk.

A third embodiment of the present invention is illustrated in FIG. 4. Those elements referenced by numbers identical to FIGS. 2 and 3 perform the same or similar function. In the FIG. 4 embodiment, the sealing disk 60 is formed to include an annular trough 76 located between inner sidewall 70 and outer sidewall 72. In this embodiment, O-ring 62 is located within annular trough 76.

Although the invention has been described in detail with reference to certain preferred embodiments, variations and modifications exist within the scope and spirit of the present invention as described and defined in the following claims.

What is claimed is:

1. In a calibrated gas metering valve including a valve body having a gas inlet and a gas outlet, and a metering element located therebetween, the metering element including a passageway formed therethrough to permit gas flow through the passageway from the gas inlet to the gas outlet, the improvement comprising:

a cylindrical sealing disk formed to include an aperture aligned with the passageway and the gas inlet to permit gas flow through the sealing disk, the sealing disk providing a plastic seal abutting and extending between the valve body and the metering element, the sealing disk being formed to include a recessed portion surrounding the aperture; and an O-ring located in the recessed portion of the sealing disk.

2. The improvement of claim 1, wherein the metering element is formed to include a plurality of passageways for gas flow from the gas inlet to the gas outlet, the metering element being movable with respect to the valve body and gas inlet to align a selected passageway in communication with the gas inlet, the sealing disk being located in a fixed position relative to the valve body so that the metering element slides over the sealing disk as the metering element moves relative to the valve body thereby sealing the selected passageway.

3. The improvement of claim 1, wherein the sealing disk includes an inner wall defining the aperture and an outer wall, the recessed portion for receiving the O-ring being formed in the sealing disk adjacent the inner wall.

4. The improvement of claim 1, wherein the sealing disk includes an inner wall defining the aperture and an outer wall, the recessed portion for receiving the O-ring being formed in the sealing disk adjacent the outer wall.

5. The improvement of claim 1, wherein the sealing disk includes an inner wall defining the aperture and an outer wall, and wherein the recessed portion is an annular trough formed in the sealing disk between the inner and outer walls for receiving the O-ring.

6. The improvement of claim 1, wherein the sealing disk is formed from a plastic material.

7. The improvement of claim 6, wherein the sealing disk is formed from tetrafluoroethylene.

8. The improvement of claim 1, wherein the O-ring is a carboxylated nitrile O-ring.

9. A gas metering valve for selectively providing a series of different calibrated gas flow rates, the valve comprising:

a valve body having a gas inlet, a gas outlet, a chamber situated between the gas inlet and gas outlet;

a metering element located in the chamber, the metering element being formed to include a plurality of passageways for permitting gas flow from the gas inlet to the gas outlet, the metering element being movable relative to the valve body to position a selected passageway in communication with the gas inlet; and a seal apparatus including a plastic sealing disk in sliding contact with the metering element and abutting the valve body, the sealing disk having an aperture formed therethrough aligned with the gas inlet for sealing said chamber against the transmission of gas therethrough except when the metering element is oriented with the selected passageway in registry with the aperture in the sealing disk, the sealing disk also being formed to include a recessed portion surrounding the aperture, the seal apparatus also including an O-ring located in the recessed portion of the sealing disk for engaging the metering element.

10. The gas metering valve of claim 9, wherein the metering element is cylindrical and rotatable within the chamber of the valve body about an axis of rotation, the plurality of passageways being arranged about the axis of rotation and extending linearly through the cylindrical metering element parallel to the axis of rotation.

11. The improvement of claim 9, wherein the sealing disk includes an inner wall defining the aperture and an outer wall, the recessed portion for receiving the O-ring being formed in the sealing disk adjacent the inner wall.

12. The improvement of claim 9, wherein the sealing disk includes an inner wall defining the aperture and an outer wall, the recessed portion for receiving the O-ring being formed in the sealing disk adjacent the outer wall.

13. The improvement of claim 9, wherein the sealing disk includes an inner wall defining the aperture and an outer wall, and wherein the recessed portion is an annular trough formed in the sealing disk between the inner and outer walls for receiving the O-ring.

14. The improvement of claim 9, wherein the sealing disk is formed from a plastic material.

15. The improvement of claim 14, wherein the sealing disk is formed from tetrafluoroethylene.

16. The improvement of claim 9, wherein the O-ring is a carboxylated nitrile O-ring.

* * * * *